United States Patent [19]

Müller

[11] 4,156,630
[45] May 29, 1979

[54] PROCESS AND APPARATUS FOR CARRYING OUT A FERMENTATION OPERATION UPON RECYCLING OF MICROORGANISMS

[76] Inventor: Hans Müller, Im Allmendli, CH-8703 Erlenbach, Switzerland

[21] Appl. No.: 796,877

[22] Filed: May 16, 1977

[30] Foreign Application Priority Data

May 18, 1976 [CH] Switzerland ............... 6303/76

[51] Int. Cl.$^2$ ................. C12B 1/00; C12K 1/10
[52] U.S. Cl. ................. 195/115; 195/116; 210/75; 210/76
[58] Field of Search ........... 195/115, 142, 143, 144, 195/116, 108, 109; 210/60, 75, 76

[56] References Cited

U.S. PATENT DOCUMENTS

| 2,967,107 | 1/1961 | Geiger et al. | 195/115 X |
| 3,969,190 | 7/1976 | Hise et al. | 195/142 |

*Primary Examiner*—Raymond N. Jones
*Assistant Examiner*—Robert J. Warden
*Attorney, Agent, or Firm*—Michael J. Striker

[57] ABSTRACT

In a fermentation employing microorganisms or enzymes the nutrient medium is mixed in the fermenter with a filter aid and the inoculum. After completion of the fermentation the fermentation broth is passed into a filter where it is directed through filtration elements whereby a filter cake is caused to deposit on the filtration means, which filter cake is composed of or includes the filter aid and all or a substantial part of the microorganisms or enzymes. The fermentation filtrate is then discharged while the passage of fermentation broth from the fermentor to the cake filter is suspended. A centrifugal motion is then imposed on the filter elements whereby the filter cake is loosened from the filter elements followed by recycling of the detached filter cake into the fermentor for reuse of the microorganisms or enzymes after resuming the fermentation.

13 Claims, 1 Drawing Figure

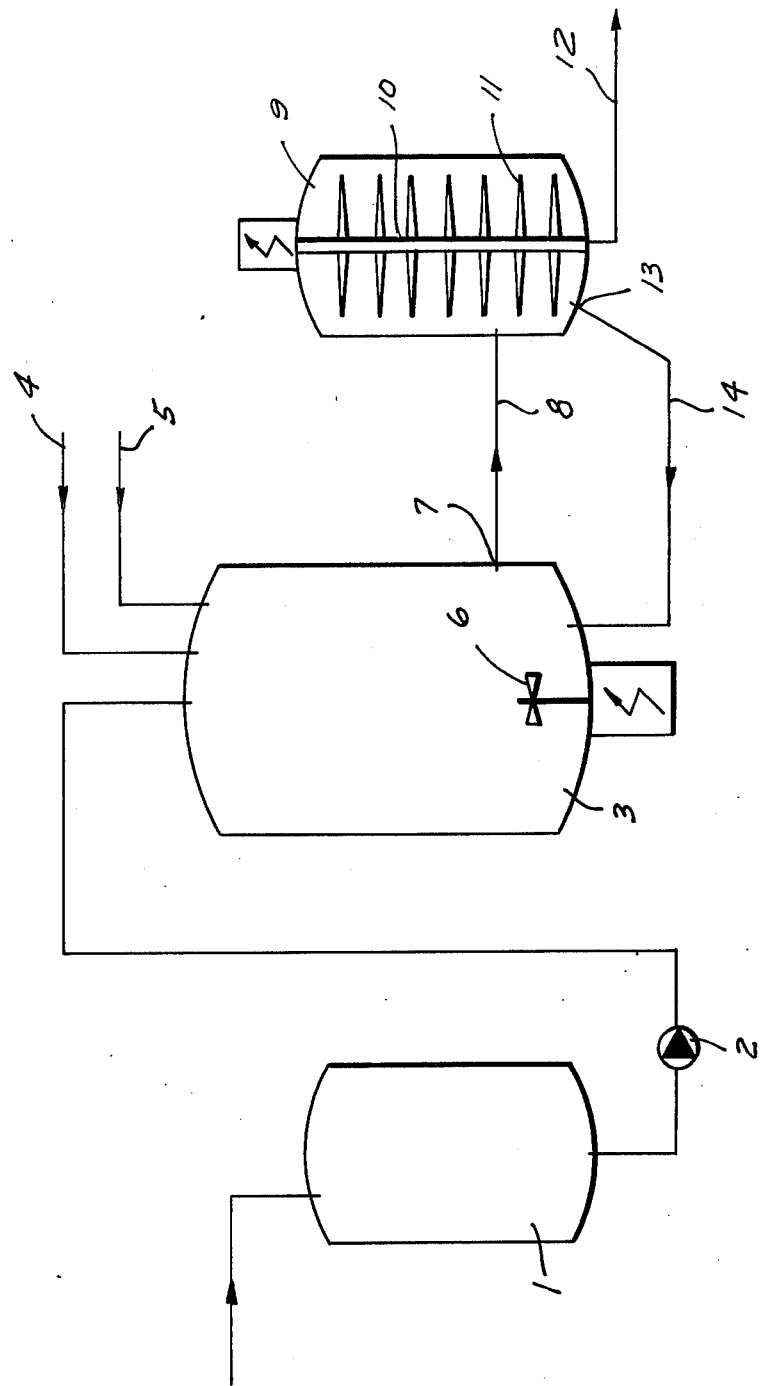

PROCESS AND APPARATUS FOR CARRYING OUT A FERMENTATION OPERATION UPON RECYCLING OF MICROORGANISMS

BACKGROUND OF THE INVENTION

The invention relates to a process of fermentation wherein the microorganisms or enzymes are recycled into the fermentor after separating therefrom the fermentation filtrate.

Processes for recycling concentrated microorganisms in order to increase the cell concentration in the fermentor are known. Such recycling operation is for instance carried out when making yeast by dehydrating the fermented substrate received from the fermentor together with the yeast by means of centrifuges. The yeast cells are thus separated by the centrifugal force from the spent nutritive medium. The yeast can then be recycled as a 16 to 20% aqueous suspension into the fermentor or can be used otherwise.

However, where the microorganisms are bacteria which are to be recycled, the separation is frequently very difficult because of the size of the microorganisms which is smaller by a full digital point. In this case the water removal must be accomplished by using ultra centrifuges.

If in this case there is still some degree of a closed system of recycling by means of centrifuges, this is definitely no longer possible where the yeasts are separated by vacuum rotary filters. Bacteria can be separated in this manner only after preceding coagulation, which means killing the bacteria.

Another shortcoming of all of these processes is that operation under sterile conditions is very difficult and frequently hardly possible under conditions of industrial use.

It is therefore an object of the invention to provide for a process for recycling and concentrating microorganisms into the fermentor which preferably is carried out under sterile conditions.

SUMMARY OF THE INVENTION

These objects are met by a fermentation process wherein a filter aid is added to the nutrient medium and inoculum in the fermentor whereupon, after carrying out the fermentation, the fermentation broth is passed into a filter where a filter cake formed on filter plates essentially consists of the filter aid and the microorganisms and enzymes used in the filtration operation. The passage of the fermentation broth is then temporarily suspended after discharging the fermentation filtrate from the filter and a centrifugal motion is imposed on the filter plates whereby the filter cake is loosened therefrom. The detached filter cake containing the microorganisms or enzymes is then recycled into the fermentor for further use after resuming the fermentation operation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The drawing in a schematic manner illustrates the process of the invention and an apparatus used therein.

DETAILS OF THE INVENTION AND DESCRIPTION OF A PREFERRED EMBODIMENT

The filter aides used in the process of the invention are particularly those which have a low degree of abrasion. Particularly suitable are cellulosic filter aids such as the filter aide sold under the trade name "SolcaFloc" by the Brown Co. of New York City, and the filter aide sold by the Celcommerz Co. of Ellwangen of Germany, under the trade name "Diacel." Also, a pulverulent cellulosic filter aid may be used, such as sold by the Eagle-Picher Co. of Cincinnati, Ohio, under the trade name "Celatom type PB33."

In general the filter aids may be granular or fibrous materials capable of forming filter cakes, and they may be used in amounts between about 0.5 and 30 g/l of fermentation broth depending on the type of microorganisms. Preferably, the filter aids are used in an amount equal to the dry mass of microorganisms in the fermentation broth.

Cellulosic materials are particularly suited because of their low abrasion effect in the fermentor and the pumps.

The filter itself may be a cake filter of the centrifugal evacuation type. A preferred type of such filter is disclosed in applicant's U.S. Pat. No. 3,251,468.

The process is suited for all kinds of microorganisms such as Acetobacter sp., Lactobacilli sp. and Pseudomonas sp.

Instead of microorganisms it is also possible to operate the process with free adsorbable enzymes. In general all kinds of bacteria which form water-soluble metabolic products may be used. In case of an enzymation reaction bacteria can also be used which form extracellular enzymes.

The process is suited for many different types of fermentation reaction such as the fermentative oxidation of sorbose to 2-keto-L-gulonic acid, the conversion of lactose into galactose and glucose by means of *Escherichia coli,* and the conversion of dextrose into fructose with a carrier supported phosphorhexo-isomerase.

Where an enzymation action is used the free enzymes to a large extent pass into the filtrate. However, a portion of the enzymes will still be adsorbed by the filter aid and the microorganism cells and thus can be recirculated and can increase the inoculum concentration.

The process can be carried out as a continuous or discontinuous operation. The process makes it possible to maintain a high cell concentration in the fermenter and thus improves the economics of the fermentation process. After completion of the fermentation cycle the filter aid may be removed together with the microorganisms from the circulation.

The apparatus employed in the invention will now be described with reference to the attached drawing.

In a culture medium tank 1 the nutrient media are mixed with a source of carbon. The sterilized culture medium is then conveyed from the tank 1 by means of the pump 2 into the fermentor 3.

At the inception of the fermentation a filter aid is added through the duct 4 and the inoculum is introduced through the duct 5. The filter aid may be subjected to sterilization prior to the introduction of the inoculum.

The fermentation can then be carried out with or without addition of air depending on the type of fermentation.

The fermentor is equipped with a stirrer 6 and an outlet 7 is provided for the fermentation product. A passage 8 permits to pass the fermentation product into the filter tank 9.

The filter, as shown, e.g., in applicant's U.S. Pat. No. 3,251,468, is a centrifugal evacuation filter. In its tank there is provided a hollow axle 10 on which the filter elements 11 are disposed. Each filter element comprises a filter web which is stretched above the base portion forming a cavity between web and base. The cavity is in communication with the hollow axle 10. A discharge duct 12 is provided for the clear filtrate while the concentrate formed in the filter as will be described below is discharged through the outlet 13 to which the recycling passage 14 is connected which leads back to the fermentor 3. Thus, a feedback is provided between the filter 9 and the fermentor 3.

The operation of the process is as follows, it being understood that the process may be carried out in a continuous or discontinuous operation as already noted.

For a continuous operation nutrient medium is continuously passed into the fermentor and the fermentation product is continuously discharged through the outlet 7 and passed through the connecting line 8 in the form of a fermented suspension into the filter 9. The filtrate, after passing through the web on the filter plates 11, flows into the hollow axle 10 through inlet apertures provided thereon and is then channeled out of the tank through the duct 12 substantially free of all microorganisms.

The inert filter aid which forms part of the suspension formed in the fermentor, together with the microorganisms, goes into the filter cake which deposits on the web of the plates 11 of the filter. Once the filter cake has reached the desired thickness, the passage of fermentation broth from the fermentor is suspended and the filter cake is loosened by subjecting the filter to a centrifugal action. The detached filter cake containing the microorganisms is then passed back as a slurry through the outlet 13 and passage 14 into the fermentor 3.

As will be seen the entire operation takes place in a closed circuit and therefore the operation can easily be carried out under sterile conditions.

In case of the use of free adsorbable enzymes the enzymated product instead of a clear filtrate as obtained with microorganisms will be discharged through the duct 12.

The following illustrates a specific use of the process of the invention.

EXAMPLE

This example relates to the fermentative oxidation of sorbose to 2-keto-L-gulonic acid, an intermediate product for the vitamin C synthesis. The microorganisms which may be used in this process belong to the Genera Pseudomonas and Acetobacter. A process of this type is described in U.S. Pat. No. 3,234,105.

For the purpose of the fermentation a nutritive base medium was formed in the mixing tank. The medium consisted of 5% sorbitol, 0.5% glucose, 0.5% yeast extract and 1 to 2% calcium carbonate ($CaCO_3$).

The mixing and sterilization of the nutrient medium was effected in conventional manner in a mixing tank. 30 l of the nutrient medium were then pumped into a fermentor of 50 l contents which previously had been sterilized by steam at 121° C. during half an hour. The fermentor was then inoculated with 500 ml inoculum consisting of Acetobacter sp. and about simultaneously 2 to 3 g/l of sterile filter aides were added into the fermentor in the form of a suspension.

The fermentation was then carried out at a temperature of 28° to 30° C. at 580 to 600 rpm. The aeration was effected with 0.5 to 0.8 vvm.

After about 150 hours the contents of the fermentor were transferred in sterile form and under sterile conditions into the centrifugal evacuation filter. The cells and the filter aid were then separated from the clear solution by the filter web and were caused to deposit as a filter cake on the filter plates while the solution passed into the hollow axle and into the discharge duct.

There were obtained 25 to 27 l of clear filtrate from which 5 g/l of 2-keto-L-gulonic acid were isolated.

The filter cake was then ripped off the filter plates by means of a centrifugal action imposed upon the plates and was recycled as a slurry into the fermentor. A reoculation of the fermentor was not necessary since the microorganisms had retained their full vitality.

Other products which may be formed in a similar manner are lactic acid which may be obtained from lactose by means of lactobacilli or the oxidation products of naphthalene which may be obtained by means of Pseudomonas sp.

Examples of enzymation reactions involving bacteria which form extracellular enzymes have been given above.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The average size of the filter particles is in the range of between 25 and 250 microns.

What is claimed as new and desired to be protected by Letters Patent is set forth in the appended claims:

1. A process of fermentation wherein the microorganisms or enzymes used in the fermentation are recycled, the said process comprising
 passing a nutrient medium, a cellulosic filter aid and an inoculum into a fermentor,
 effecting the fermentation in the fermentor under fermentation conditions,
 then passing the fermentation broth into a filter tank and through filter elements disposed therein, thereby causing a filter cake to be deposited on the filter elements, the said filter cake being composed of or including said filter aid and all or a substantial part of said microorganisms or enzymes,
 discharging the fermentation filtrate, which passes through said filter elements,
 thereafter suspending the passage of fermentation broth from the fermentor into the filter tank,
 then imparting a centrifugal action to the filter elements, thereby loosening the filter cake therefrom, and
 recycling the detached filter cake into the fermentor for reuse of the microorganisms or enzymes after resuming the fermentation operation.

2. The process of fermentation of claim 1 wherein the filter aid is a granular, fibrous or pulverulent cellulosic material.

3. The process of claim 1 wherein the filter aid is employed in an amount between 0.50 and 30 g/l of fermentation broth.

4. The fermentation process of claim 1 wherein the filter aid is employed in an amount about equal to the dry matter of microorganisms in the inoculum.

5. The fermentation process of claim 1 wherein the microorganisms employed are selected from the group Acetobacter sp., Lactobacilli sp. and Pseudomonas sp.

6. The fermentation process of claim 1 wherein the inoculum is composed of bacteria forming extracellular enzymes.

7. The fermentation process of claim 1 wherein the nutrient medium is premixed before passing into the fermentor whereupon the filter aid and inoculum are introduced in the fermentor.

8. The fermentation process of claim 1 wherein the nutritive medium and filter aid are subjected to sterilization prior to fermentation.

9. The fermentation process of claim 1 wherein the fermentation broth and filter cake move on a closed path subject to sterile conditions throughout the fermentation, filtration and recycling operation.

10. The fermentation process of claim 1 wherein the fermentation is carried out with free enzymes of which a substantial part is subjected to said recyclization step.

11. An apparatus for use in a fermentation process wherein the microorganisms and enzymes employed in the fermentation are at least partly recycled, the said apparatus comprising

[a] a fermentor;
[b] means for passing a culture medium into the fermentor;
[c] means for adding a filter aid to the culture medium in the fermentor;
[d] means for introducing an inoculum into the fermentor;
[e] means for maintaining fermentation conditions in said fermentor;
[f] a filtration tank;
[g] a passage for the fermentation broth from the said fermentor to the said filtration tank;
[h] a plurality of generally horizontal filter plates disposed in said filter tank and having surfaces for permitting a filter cake to form thereon;
[i] an outlet in said filtration tank for discharging the filtrate;
[j] means for imposing a centrifugal force on said filter plates whereby the filter cake disposed thereon is loosened from the plates, and
[k] a passage connecting the lower portion of said filter tank with said fermentor for recycling said filter cake after its detachment from said filter plates.

12. The apparatus of claim 11 wherein a separate mixing tank is provided for said culture medium and a passage and pump means are provided for passing the culture medium into the fermentation tank.

13. The apparatus of claim 11 wherein the filtration tank is provided with a hollow center shaft, the said filter plates being carried by said shaft, and wherein inlets are provided for leading the filtrate which passes through the filter surface into said hollow shaft, the said outlet for the filtrate being disposed at the bottom end of said center shaft.

* * * * *